US012661264B2

(12) United States Patent
Hacker et al.

(10) Patent No.: US 12,661,264 B2
(45) Date of Patent: Jun. 23, 2026

(54) STENT IMPLANT FOR TREATING GLAUCOMA BY MEANS OF INTRAOCULAR FLUID DRAINAGE FROM THE ANTERIOR CHAMBER

(71) Applicant: Carl Zeiss Meditec AG, Jena (DE)

(72) Inventors: Martin Hacker, Jena (DE); Martin Kuehner, Bad Klosterlausnitz (DE)

(73) Assignee: Carl Zeiss Meditec AG, Jena (DE)

( * ) Notice: Subject to any disclaimer, the term of this patent is extended or adjusted under 35 U.S.C. 154(b) by 492 days.

(21) Appl. No.: 18/043,941

(22) PCT Filed: Sep. 1, 2021

(86) PCT No.: PCT/EP2021/074156
§ 371 (c)(1),
(2) Date: Mar. 3, 2023

(87) PCT Pub. No.: WO2022/049140
PCT Pub. Date: Mar. 10, 2022

(65) Prior Publication Data
US 2023/0218441 A1 Jul. 13, 2023

(30) Foreign Application Priority Data

Sep. 4, 2020 (DE) ..................... 10 2020 211 175.8

(51) Int. Cl.
*A61F 9/007* (2006.01)
*A61F 2/82* (2013.01)
(52) U.S. Cl.
CPC ............ *A61F 9/00781* (2013.01); *A61F 2/82* (2013.01); *A61F 2230/006* (2013.01)
(58) Field of Classification Search
CPC .. A61F 9/00781; A61F 2/82; A61F 2230/006; A61F 2230/0063; A61F 2009/00891
See application file for complete search history.

(56) References Cited

U.S. PATENT DOCUMENTS 3,788,327 A 1/1974 Donowitz et al.
6,881,198 B2 4/2005 Brown
(Continued)

FOREIGN PATENT DOCUMENTS

DE 10103000 8/2002
DE 102015108835 12/2016
(Continued)

OTHER PUBLICATIONS

International Search Report (English Translation provided) and Written Opinion for PCT/EP2021/074156 date mailed Dec. 23, 2021.

(Continued)

*Primary Examiner* — Leslie R Deak
(74) *Attorney, Agent, or Firm* — DeWitt LLP

(57) ABSTRACT

A stent implant for treating glaucoma by intraocular fluid drainage from the anterior chamber, for example into the suprachoroidal space. The stent implant is designed to change in shape after being inserted into the eye, during which change the width and/or thickness or the flow cross-section is increased by for example 20%, in another example more than 200%, and in a further example by more than 400%, at least one point of the stent implant. In the case of intraocular fluid drainage from the anterior chamber into the suprachoroidal space, a cyclodialysis cleft which may open can be largely or completely closed. With appropriate adjustments, the stent implant can also be applied in trabecular, uveoscleral, uveolymphatic and subconjunctival applications for intraocular fluid drainage from the anterior chamber. The implant can even be used for direct intraocular fluid discharge from the anterior chamber onto the surface of the eye.

20 Claims, 4 Drawing Sheets

(56) References Cited

U.S. PATENT DOCUMENTS

| | | | |
|---|---|---|---|
| 8,925,510 B2 | 1/2015 | Stec et al. | |
| 8,926,510 B2 | 1/2015 | Marshall et al. | |
| 2004/0193262 A1 | 9/2004 | Shadduck | |
| 2004/0260228 A1 | 12/2004 | Lynch et al. | |
| 2005/0192527 A1* | 9/2005 | Gharib ..................... | A61B 3/16 604/8 |
| 2008/0039920 A1 | 2/2008 | Peacock et al. | |
| 2012/0035524 A1 | 2/2012 | Silvestrini | |
| 2018/0125710 A1 | 5/2018 | Schachar et al. | |
| 2018/0128710 A1 | 5/2018 | Schachar et al. | |
| 2020/0078218 A1 | 3/2020 | Holland et al. | |

FOREIGN PATENT DOCUMENTS

| | | |
|---|---|---|
| EP | 3403622 | 11/2018 |
| WO | WO2004110391 | 12/2004 |
| WO | WO2008008253 | 1/2008 |
| WO | WO 2011/032526 A1 | 3/2011 |
| WO | WO2011032526 | 3/2011 |
| WO | WO2011097408 | 8/2011 |
| WO | WO 2014/049174 A1 | 4/2014 |
| WO | WO2014049174 | 4/2014 |
| WO | WO2016109639 | 7/2016 |
| WO | WO2017108498 | 6/2017 |

OTHER PUBLICATIONS

He, Zheng, et al., "The Rold of Blood Pressure in Glaucoma", Clinical and Experimental Optometry (2011); 94:2: pp. 139-149.

Denis MD, Philippe, et al., "A First-in-Human Study of the Efficacy and Safety of MINIject in Patients with Medically Uncontrolled Open-Angle Glaucoma (STAR-I)", American Academy of Ophthalmology, vol. 2, Issue 5, September-Oct. 2019, pp. 290-297.

Saheb, Hady et al., "Optical Coherence Tomography of the Suprachoroid after CyPass Micro-Stent Implantation for the Treatment of Open-Angle Glaucoma", Br J Ophthalmology (2013); 00:1-5.

Del Valle-Nava, F., et al., "Management of Persistent Hypotony after Supraciliary CyPass® Implantation Using Argon Laser", Journal of Current Glaucoma Practice, vol. 13, Issue 3 (September-Oct. 2019); pp. 116-118.

International Preliminary Report on Patentability for PCT/EP2021/074156 dated Mar. 7, 2023, 7 pages.

* cited by examiner

STENT IMPLANT FOR TREATING GLAUCOMA BY MEANS OF INTRAOCULAR FLUID DRAINAGE FROM THE ANTERIOR CHAMBER

RELATED APPLICATIONS

This application claims priority from Application PCT/EP2021/074156, filed Sep. 1, 2021, and claims priority from DE Patent Application No. 10 2020 211 175.8 filed Sep. 4, 2020 each of which are incorporated by reference in their entireties in this application.

TECHNICAL FIELD

Embodiments of present invention relates to a stent implant for treating glaucoma by drainage of aqueous humor from the anterior chamber, for example into the suprachoroidal space.

BACKGROUND

Such implants for drainage of liquid are well known in the prior art. While what are referred to as stents are usually understood as being drainage aids for opening or for keeping open vessels or tissues, what are referred to as shunts serve as drainage aids for bridging, or bypassing, natural drainage paths. However, these functions can also be applied simultaneously or can overlap. According to the invention, the term used below, stent, can thus comprise both functions.

Glaucoma, or sometimes referred to as green star, is understood to mean a disease leading to irreversible damage to the optic nerve fibers. In advanced stages, it is even possible for excavation of the optic nerve to occur. Continuously progressing damage to the optic nerve causes a similarly continuous decrease in the field of vision of the patient. Without treatment, this in most cases leads to complete loss of sight.

Although the number of all possible causes of glaucoma or of the described damage to the optic nerve is not fully understood at present, one of the most important triggers has been identified as an increase in intraocular pressure caused by deterioration in the drainage of aqueous humor within the eye.

As a consequence of this deterioration in the drainage of aqueous humor, i.e. the increased drainage resistance, the pressure within the eye builds up until, with the intraocular pressure now increased, the drainage of aqueous humor is once again in equilibrium with the production of aqueous humor. The relationship between the pressure drop ΔP that arises over the drainage pathways, given an existing throughflow resistance R and an aqueous humor flow Q, is $\Delta P = R*Q$.

The changed pressure conditions are then suspected of causing direct damage to the optic nerve through mechanical action, and/or of causing a reduction in the perfusion pressure, which is important for supplying the optic nerve fibers, in the retina as a result of a changed pressure drop.

A deterioration in the drainage of aqueous humor can be caused, for example, by a narrowing of the iridocorneal angle (narrow-angle glaucoma) or, in the case of open-angle glaucoma, by changes to the filter tissue of the trabecular meshwork or even the complete blockage thereof (for example in the case of pseudoexfoliation glaucoma or pigmentary glaucoma), or as a result of a reduction in the cross section of Schlemm's canal or of downstream collector vessels or in the episcleral vascular system. Changes to tissues in the uveoscleral outflow pathway may also lead to deterioration in the drainage of aqueous humor. Recent investigations also point toward the influence of a third outflow pathway, the uveolymphatic outflow pathway.

If damage to the optic nerve fibers occurs when the intraocular pressure appears to be normal, reference is also made to normal pressure glaucoma. It is assumed that, in this case, unfavorable blood pressure conditions (in particular in the event of very low blood pressure) also result in reduced perfusion pressures, which then cause damage to the optic nerve fibers. The results of the investigations of Zheng He et al. has been documented in [1].

A treatment approach under consideration in the treatment of glaucoma is in most cases the reduction of the intraocular pressure. In rarer cases, however, the blood pressure is also adapted.

In the first instance, the intraocular pressure is usually reduced by medication, i.e. using substances which either reduce the production of aqueous humor (for example beta blockers) or else improve drainage through the tissues of the drainage pathways (for example prostaglandins). In recent developments, it is also already the case that prostaglandin analogs (bimatoprost) are embedded in biodegradable polymers and used as implantable medication repository for treating glaucoma (bimatoprost SR with the polymer system poly(D,L-lactide), poly(D,L-lactide-co-glycolide), poly(D,L-lactic acid) and polyethylene glycol 3350).

In addition, an improvement in the trabecular drainage can also be obtained through laser trabeculoplasty procedures (selective laser trabeculoplasty (SLT), argon laser trabeculoplasty (ALT), excimer laser trabeculoplasty (ELT)). In that respect, US 2020/078218 A1, inter alia, also proposes a trabecular meshwork treatment by application of femtosecond lasers.

Moreover, canaloplasty procedures in which Schlemm's canal is widened are known. If the glaucoma worsens, sometimes a trabeculotomy (partial excision of the trabecular meshwork) or partial coagulation of the aqueous-humor-producing ciliary body tissue is considered, for example in the form of cyclophotocoagulation (CPC), cyclocryocoagulation (CRC) or ultrasonic cyclocoagulation (UCC).

If these measures cannot be used or are inadequate, recourse is then usually made to filtration surgery, for example in the form of a trabeculectomy, in which an artificial drainage path into a bleb is formed under the connective tissue.

To treat advanced green star, a trabeculectomy is considered the standard procedure, although the rate of complications resulting from reactions by the body (scarring) is relatively high, the scarring process has to be controlled by intraoperative use of antifibrotic agents and, in many cases, follow-up measures (needling) are still required.

In addition, use is made of yet larger implants (tube shunts)

in which aqueous humor is conveyed from the anterior chamber through a tube to a drainage plate which is secured on the sclera, but underneath connective tissue, usually by suturing, and from which the aqueous humor is conveyed into a bleb under the eye surface (Baerveldt implant, inter alia). A problem with tube shunts is that the capacity of the tissue lining the bleb to take up aqueous humor considerably changes as a result of the suturing processes used. As a result, in the first few weeks after the implantation, transient hypotonia (temporary drop in intraocular pressure) can occur, before the outflow pathway artificially provided by the bleb stabilizes. This transient hypotonia is usually counteracted by using wound-modulating substances (antifibrotic agents) or covering materials (for example from the pericardium), and also through transitional suture or else blockage of the tube by use of a surgical thread over several weeks. These implants can additionally have valve effects too (Ahmed valve) or, more recently, also be adjustable (Rheon eyeWatch).

In the prior art, other surgical forms of glaucoma treatment with reduced invasiveness have also become known in recent years (micro-invasive glaucoma surgery or micro-incision glaucoma surgery, or in short: MIGS), these being intended to have a greater potential for pressure reduction along with reduced rates of complications, for example through the use of minimally invasive stents and shunts (for example for bridging the trabecular meshwork and for keeping open Schlemm's canal (iStent, HYDRUS) or for drainage from the anterior chamber into the supraciliary space, or suprachoroidal space (CYPASS, MINIject, iStent Supra) or into the subconjunctival space (XEN, MicroShunt). Stents for the suprachoroidal space typically have lengths of 4 to 6.4 mm and implant widths of 0.43 mm (CYPASS, round) through approximately 1 mm (MINIject, rectangular with rounded corners) to approximately 5 mm (STARflo, planar). The latter, however, is usually no longer considered to be a MIGS device, since it cannot be introduced into the eye with minimal invasion. Thicknesses of suprachoroidal implants are between 0.43 mm (CYPASS) and 0.6 mm (MINIject).

Article [2] contains a study on the effectiveness and safety of MINIject implants in the case of open-angle glaucoma and, in addition to the geometry of the implant, also describes that the implant protrudes approximately 0.5 mm into the anterior chamber after implantation. As is known from other suprachoroidal implants, implants that protrude too far (i.e. 1-2 mm) into the anterior chamber are suspected of contributing to losses of endothelial cells in the cornea, which must be avoided.

The abovementioned surgical interventions are classed as ab interno or ab externo interventions, depending on whether the manipulation or the implantation is performed from inside the eye or from outside the eye.

For example, canaloplasty procedures can be performed as ab interno or ab externo interventions. Examples of stents that can be implanted ab interno are iStent, HYDRUS, CYPASS and XEN, while the MicroShunt is an example of a stent or shunt that can be implanted ab externo.

By contrast to the drainage of aqueous humor from the anterior chamber, also possible in principle is drainage from the eye posterior chamber (for example via tube lead-throughs through the iris), but this would very probably entail damage to important eye structures which contribute either to the vision process (iris, crystalline lens or retina) or to the production of aqueous humor (ciliary body).

Glaucoma stents or shunts can consist of non-porous materials, for example nitinol, steel, titanium, polyamides, polyethylene glycol and polyurethane (WO 2004/110391 A1), or porous materials, such as biocompatible porous silicones (WO 2017/108498 A1), but can also consist of combinations of these and also contain sensors, for example for the intraocular pressure (U.S. Pat. No. 8,926,510 B2).

An example of a tool for ab interno implantation of a porous implant in the suprachoroidal space is disclosed in WO 2017/108498 A1. In that document, before implantation the implant is compressed somewhat in the hollow tool shaft and correspondingly expands again somewhat after ejection. Another example of a tool for ab interno implantation of a tubular implant in the suprachoroidal space is disclosed in EP 3 403 622 B1.

Reference is also made by way of example to documents U.S. Pat. No. 6,881,198 B2 and U.S. Pat. No. 3,788,327,
    which describe corresponding surgical implants for reducing
    the intraocular pressure by draining excess
    aqueous humor. These surgical implants in the form of stents utilize
    direct drainage through the cornea, the limbus or the sclera. These stents
    may contain a filter membrane in order to ensure a defined outflow, and filters for retaining disruptive particles.
    WO 2016/109639 A2 also describes devices for treating glaucoma, but the focus in that document is on additional measures for securely anchoring stents of that type in the tissue.

Stents for suprachoroidal use have a greater pressure reduction effect than stents for trabecular use and have the advantage over stents for subconjunctival use that they do not cause damage to the connective tissue and thus keep further treatment options open. Stents for suprachoroidal use also require no wound modulation through the use of substances that control scarring, such as mitomycin C.

A principal disadvantage of stents for suprachoroidal use is that the changes in pressure reduction that can be achieved are extremely difficult to predict. The problems in particular are possible transient strong pressure drops (hypotonia) or pressure increases (hypertonia)

In hypotonia (<5 mmHg), serious complications through to retinal detachment can occur. Hypertonia, on the other hand, leads to progression of the glaucoma.

The cause of the problems is usually the production, but also possible sudden closure, of a cyclodialysis cleft, torn open by the implantation, between detached ciliary muscle fibers and the scleral spur, which can result in a stronger outflow of aqueous humor from the anterior chamber directly into the suprachoroidal space.

In article [3], using the example of the CYPASS implant, Hady Saheb et al. disclose that the cleft that forms can have a width many times that of the cross section of the implant, and therefore reference is even made to "tenting" (spanning of a tent-like structure).

As described by Fernando Del Valle-Nava et al. in [4], in practice such cases must sometimes even be treated by laser coagulation, to be able to control them.

Although in the past cyclodialysis clefts were deliberately created in surgical procedures for reducing the intraocular pressure, nowadays they are used less and less on account of it being difficult to be able to predict the pressure reduction.

LITERATURE

[1] He, Z. et al.; "The role of blood pressure in glaucoma", Clin Exp Optom 2011; 94: 2: 133-149

[2] Denis, P. et al.; "A First-in-Human Study of the Efficacy and Safety of MINIject in Patients with Medically Uncontrolled Open-Angle Glaucoma (STAR-I)"; Ophthalmology Glaucoma Volume 2, Number 5, September/October 2019; 290-297

[3] Saheb, H, et al.; "Optical coherence tomography of the suprachoroid after CyPass Micro-Stent implantation for the treatment of open-angle glaucoma"; Br J Ophthalmol 2013; 00:1-5

[4] Del Valle-Nava, F. et al.; "Management of Persistent Hypotony after Supraciliary CyPass® Implantation Using Argon Laser"; Journal of Current Glaucoma Practice, Volume 13 Issue 3 (September-December 2019); 116-118.

SUMMARY OF THE INVENTION

Embodiments of the present invention include producing a stent implant for treating glaucoma by drainage of aqueous humor from the anterior chamber, for example into the suprachoroidal space, which stent implant achieves pressure reductions which are as consistent as possible. In particular, the stent implant should be suitable for closing a wide cleft that has possibly opened up in the suprachoroidal space such that no outflow, or only limited outflow, of aqueous humor outside of the implant can occur.

A stent implant for treating glaucoma by drainage of aqueous humor from the anterior chamber is designed to change shape after introduction into the eye, which change involves increasing the width and/or thickness or the throughflow cross section at least at one point on the stent implant by for example more than 20%, in another example more than 200% and in a further example by more than 400%. This change could of course also be realized at multiple points on the implant. In the event of drainage of aqueous humor from the anterior chamber into the suprachoroidal space, this makes it possible to largely or completely fill in or to at least largely close a cyclodialysis cleft that has possibly opened up. By increasing a throughflow cross section, it is possible to boost inadequate drainage, since an increase in the throughflow cross section reduces the resistance to the flow of aqueous humor through the implant.

First example embodiments relate to the change in shape of the stent implant, in particular the increase in its width and/or thickness, and the change in the resistance to the throughflow of aqueous humor when the shape changes.

Second example embodiments relate to the material used for the stent implant, which either consists of an elastic, open-pore or non-porous metal material or elastic, sponge-like, open-pore or non-porous plastics.

Further example embodiments relate to the shape and/or the cross section of the stent implant, which is modifiable in order to establish the inflow and outflow zones of the implant such that a throughflow cross section predominantly independent of the shape is achieved.

A particular example embodiment provides that, to produce a throughflow cross section that is independent of its shape, the stent implant has additionally partially or completely sealing, umbrella-like surfaces.

The proposed stent implant for treating glaucoma is intended for example for the drainage of aqueous humor from the anterior chamber into the suprachoroidal space. With corresponding adaptations, however, the stent implant can also be used for trabecular, uveoscleral, uveolymphatic and subconjunctival applications for drainage of aqueous humor from the anterior chamber, if it is also necessary to prevent undesired enlargements of the outflow cross section there that are caused by the tissue rupturing. Such adaptations to the respective outflow pathway relate for example to thicknesses, lengths, throughflow cross sections, materials, markings, side openings, but also options for securing in the tissue, as is already known for these outflow pathways from existing stents.

Use for the direct drainage of aqueous humor from the anterior chamber onto the eye surface is also possible, for example if limbus or cornea incisions (target tissue) are larger than planned and are to be closed by the implant.

BRIEF DESCRIPTION OF THE DRAWINGS

The invention is described in more detail below on the basis of example embodiments. In the figures.

DETAILED DESCRIPTION

Figure 1:
FIG. 1: depicts a selection of possible shapes of the stent implant.

According to example embodiments, the stent implant serves for example to treat glaucoma by drainage of aqueous humor from the anterior chamber into the suprachoroidal space of the eye and is designed such that, when there is a space available in the target tissue area, for example owing to a cyclodialysis cleft opening up, it substantially changes shape, this also being able to largely or completely fill in or at least largely close a wide cyclodialysis cleft.

In this respect, the stent implant according to the invention is for example inserted into the anterior chamber ab interno by opening up the cornea or the limbus with minimal invasion (micro-incision) and positioned correspondingly for the drainage of aqueous humor into the suprachoroidal space.

Micro-incisions are to be understood as small incisions of the kind customary in modern cataract surgery (MICS: micro-incision cataract surgery). These in most cases have incision widths of usually less than 1.4 mm and are configured such that, after removal of the surgical tool, the incisions automatically close again and, without the need for sutures, are sufficiently leaktight.

What are referred to as inserters, for example, which are known from modern cataract treatment or from other MIGS implants (CYPASS, iStent, MINIject, XEN), can be used to introduce the stent implant. Inserters are medical instruments which contain an object to be implanted. In the present case, the inserter contains the stent implant, which has been compressed into a compact, for example cylindrical shape.

The inserter has a trigger mechanism in order to be able to release the stent implant when the target tissue is reached. The stent implant partially or completely returns to its original shape during or after insertion into the suprachoroidal space in accordance with the available space and thus closes a cleft that has possibly opened up in the suprachoroidal space, in order to permit no outflow, or only very reduced outflow, of aqueous humor around the implant.

According to the invention, the stent implant is designed to substantially change shape after introduction into the eye, which change involves increasing the width and/or thickness or the throughflow cross section at one point on the stent implant by more than 20%, for example more than 200% and in another example by more than 400%, wherein the changes in its shape in terms of width and thickness differ by at least 50%.

In particular, the stent implant can be designed to change the resistance to the flow of aqueous humor through the stent implant by less than 50%, for example less than 20% and in another example less than 10%, when it changes shape. This is achieved by largely retaining the throughflow cross section of (open) pore or channel structures, at least for some time (days to months), upon the change in shape, which ensures a small or unchanged throughflow Q through the implant for a pressure drop ΔP that is present between the inlet and outlet of the implant. Accordingly, the flow of aqueous humor through the rupture or incision in the tissue, for example the cyclodialysis cleft, around the implant is largely stopped or at least greatly reduced, for example by more than 50%, in another example by more than 90%, as a result of its change in shape with a sealing effect. This sealing can be increased even further by further growth of the implant in the tissue.

In accordance with a first example embodiment, the stent implant, in particular its shape and/or cross section, is designed to establish the inflow and outflow zones of the implant such that a throughflow cross section predominantly independent of the shape is achieved.

For this, inflow and outflow zones of the stent implant can be established such that a throughflow cross section predominantly independent of the shape is achieved even if the stent implant assumes considerably different shapes depending on the space available (size of the cyclodialysis cleft).

In particular, the stent implant has a tubular or other shape, in particular a Y, X, U, N, A, V, W or O shape, or else also has a complex shape, for example a three-dimensional lattice.

FIG. 1 shows a selection of possible shapes for the stent implant.

In accordance with a second example embodiment, the stent implant consists of an elastic, open-pore or non-porous metal material, for example titanium, steel or nitinol.

Figure 2:
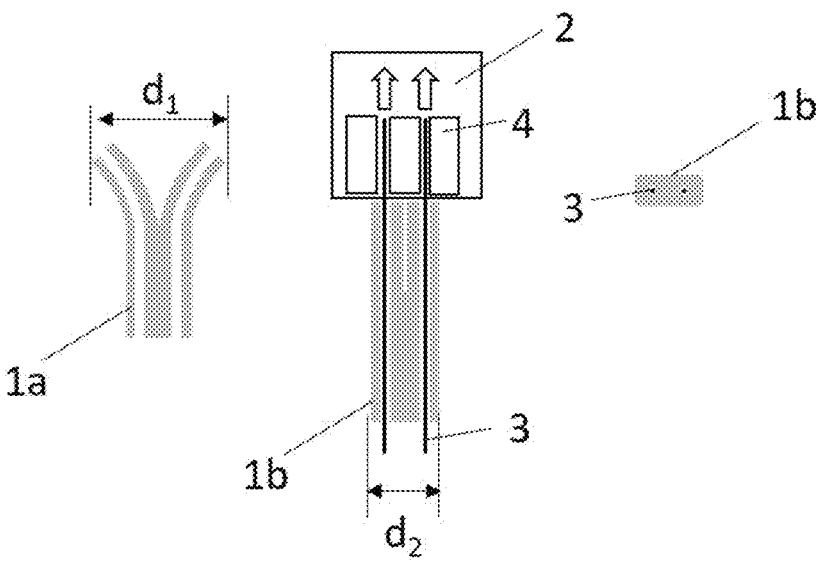
FIG. 2: depicts a Y-shaped stent implant of metal through which channels pass in the initial state, on an implantation tool in a compact shape, and in cross section to show the compact shape.

In this respect, FIG. 2 shows a Y-shaped stent implant of metal through which channels pass in its initial shape, on an implantation tool, and in cross section. Here, the material must have sufficient elasticity for the change in shape that is sought.

As can be deduced from the left-hand figure, the (expanded) initial shape $1a$ of a stent implant of an elastic metal through which channels pass has a Y shape with a width $d_1$ (when the arms are spread).

The central figure shows the Y-shaped stent implant on an implantation tool 2, which has two guide rods 3 and a holding device 4. After being placed on the implantation tool 2 (with the arms closed), the stent implant assumes a compact shape $1b$ and has only a width $d_2$.

Comparing the left-hand and middle figures, it can be deduced that the change in shape of the stent implant, from
    initial shape $1a$ with a width $d_1$ to
    compact shape $1b$ with a width $d_2$,
leads to a dimension that is reduced by $(d_1-d_2)$ and, in relation to the width $d_2$ of the compact shape, constitutes a relative reduction in dimension $(d_1-d_2)/d_2$, which is significant and exceeds 50%.

On the other hand, the stent implant is designed such that, after introduction into the eye, it can change shape, which involves increasing at least one dimension (width) given the space available (for example in a cyclodialysis cleft) such that, in relation to the dimension in the compact state, it increases by at least 20%, for example by 200% or in another example 400%.

In particular, this makes it possible to have the effect that the reduced width $d_2$ can still have a value suitable for micro-incision-based insertion of below 1.4 mm, whereas the width that can be covered in a tissue cleft after implantation can considerably exceed 1.4 mm, for example over 2.1 mm. Since cyclodialysis clefts usually have a rather planar design, it is advantageous for example if the implant changes shape mainly in one dimension, for example in that its width can change to a significantly greater extent than its thickness when it changes shape. This avoids unnecessary stress on the tissue at the same time. For example, therefore, the possible change in width of the implant is at least 50% greater than the possible change in thickness of the implant. For example, the change in shape according to the invention makes it possible to increase the width of the implant from 1.2 mm to 3.6 mm in order to close a cyclodialysis cleft, whereas the thickness changes by less than 0.1 mm. The change in width is therefore considerably greater than the change in thickness, in this case is $$\text{greater by } (2.4 \text{ mm}-0.1 \text{ mm})/0.1 \text{ mm}=2300\%.$$

The right-hand figure of FIG. 2 shows the Y-shaped stent implant $1b$ arranged on the implantation tool 2, in cross section. In this respect, the stent implant may have various cross sections, with rounded shapes for example being preferred in order to facilitate insertion of the stent implant into the target tissue.

When the target tissue is reached, the guide rods 3 can be withdrawn against the holding device 4 (as indicated by the two arrows) and the stent implant $1b$ can be detached from the implantation tool 2. After detachment from the implantation tool 2, the stent implant returns to its (expanded) initial shape $1a$ or to an intermediate state, predefined by the tissue cleft, with a width between $d_1$ and $d_2$.

For the sake of clarity, the carrier arm which is required for the ab interno implantation through the anterior chamber and has a handle for the implantation tool 2 and a retraction mechanism for guide rods 3 are not shown here. Possible embodiments for such a handle with a retraction mechanism for a guide wire is disclosed in document EP 3 403 622 B1, which has already been mentioned. Instead of withdrawing the guide rods 3 against the holding device 4, the implantation tool 2 can also have an ejection device (which is likewise not shown).

In accordance with a third example embodiment, the stent implant includes an elastic, sponge-like, open-pore or non-porous plastic, for example silicone, polyurethane or polyamide.

Figure 3:
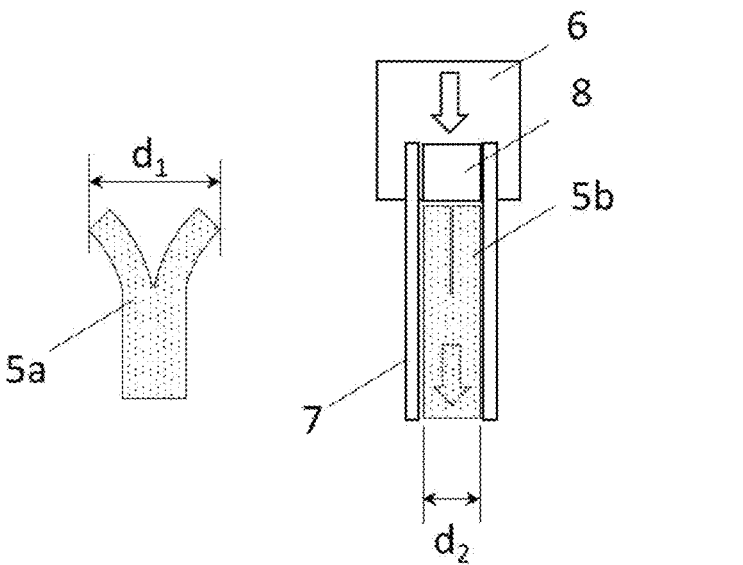
FIG. 3: depicts a Y-shaped stent implant of an elastic, sponge-like, open-pore plastic in the initial state, in an implantation tool in a compact shape, and in cross section to show the compact shape.
Figure 3:
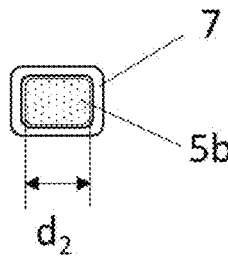

In this respect, FIG. 3 shows a Y-shaped stent implant of an elastic, sponge-like, open-pore plastic in the initial state, in an implantation tool, and in cross section.

As can be deduced from the left-hand figure, the (expanded) initial shape $5a$ of the stent implant of an elastic, sponge-like, open-pore or non-porous plastic has a Y shape with a width $d_1$ (when the arms are spread).

The central figure shows the Y-shaped stent implant in an implantation tool 6, which has a hollow shaft 7 and an ejection device 8. On the implantation tool 6 in the hollow shaft (with the arms closed), the stent implant assumes a compact shape $5b$ and has only a width $d_2$.

Comparing the left-hand and middle figures, it can also be deduced here that the change in shape of the stent implant, from initial shape 5a with a width $d_1$ to compact shape 5b with a width $d_2$, results in a reduction in dimension of more than 50%.

The right-hand figure shows the Y-shaped stent implant 5b arranged in the hollow shaft 7 of the implantation tool, in cross section, in the form of a rectangle with rounded corners. It is also possible here for the cross-sectional shape to be different, such as cylindrical, elliptical, oval, rectangular or kidney-shaped.

When the target tissue is reached, the stent implant 5b is pushed off of and detached from the shaft 7 of the implantation tool 6 by the ejection device 8 (as indicated by the two arrows). After detachment from the implantation tool 6, given available space, the stent implant returns to its (expanded) initial shape 5a here, too. Instead of an ejection device 8, the implantation tool 6 may also have a retraction device (not illustrated) for a shaft. In turn, for the sake of clarity, the tool carrier arm which is required for the ab interno implantation and the handle for triggering the ejection or retraction mechanism are not shown. Possible embodiments are disclosed, for example, in WO 2017/108498 A1.

A stent implant of an elastic, sponge-like, open-pore or non-porous plastic has the advantage that it can be produced by punching, cutting or by an injection molding process.

For example, the stent implant consists of only one plastic or of a composite of multiple plastics with different chemical and/or physical and/or mechanical properties.

In another example, the stent implant can consist completely or in certain portions of a hydrophilic plastic in order, after introduction, to cause it to change shape by taking up water.

However, it is also possible for the stent implant to use a plastic which has a memory effect, in order to cause it to change shape or adapt its shape at body temperature.

For example, the stent implant and the tool are configured such that the stent implant can be introduced in a compact shape into the eye by micro-incision (similar to a MICS cataract surgical procedure, i.e. through an incision less than 1.8 mm or even 1.4 mm in width), in order to realize ab interno implantation into the suprachoroidal target tissue on the opposite side of the anterior chamber.

In another example, the stent implant and the implantation tool are configured such that a change in shape for the purpose of closing a cyclodialysis cleft takes place only in the target tissue area after ejection or detachment from the tool.

Figure 4:
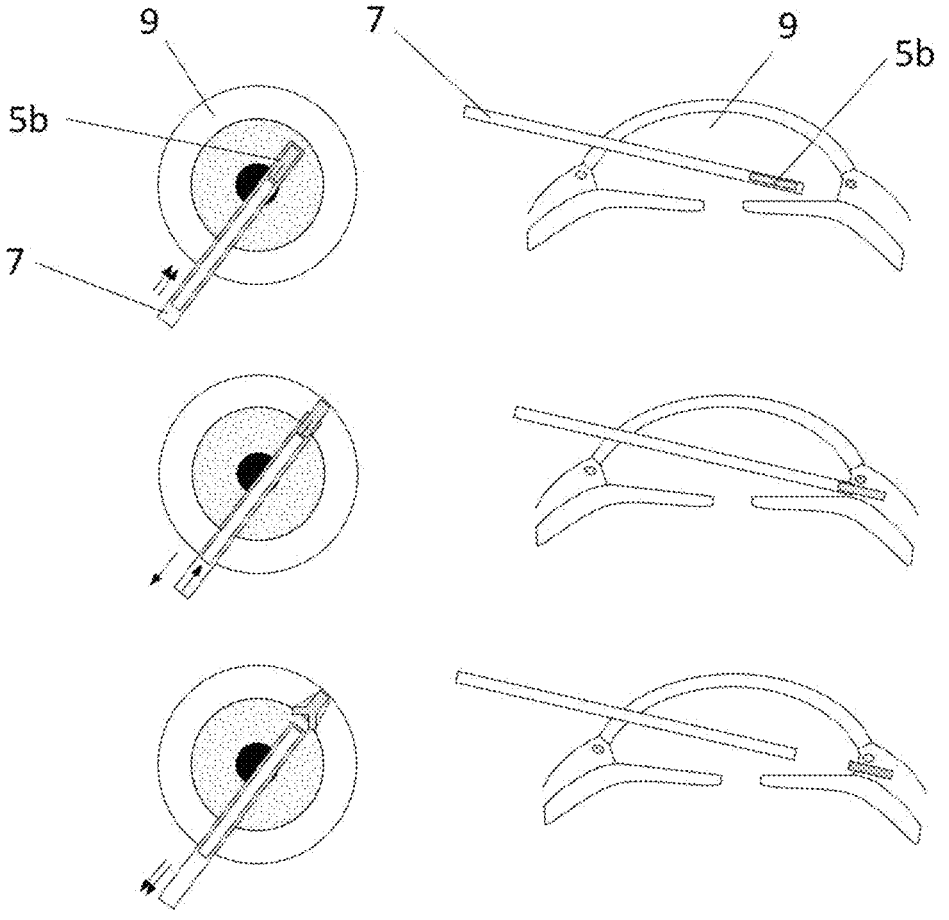
FIG. 4: depicts the phases of inserting, positioning and deploying the stent implant according to the invention.

In this respect, FIG. 4 shows the phases of inserting, positioning and deploying the stent implant according to the invention.

For this, the Y-shaped stent implant (according to FIG. 3) is arranged in its compact shape in the shaft 7 of the implantation tool 5b.

According to the upper figures, the shaft 7 of the implantation tool, together with the injection device 8 (not shown in the image) and the stent implant in its compact shape 5b (as indicated by the two arrows), is inserted into the eye 9.

The middle figures show that, when the target tissue is reached, the stent implant, which is still in its compact shape 5b, is positioned and then released in the tissue by withdrawing the shaft 7 against the ejection device 8 (as indicated by the two arrows).

The lower figures show that, after leaving the shaft 7, in the target tissue the Y-shaped stent implant assumes an expanded shape, which can be somewhere between the compact shape 5b and the maximally expanded initial shape 5a, depending on the space available in the target tissue. Then, the shaft 7 with the ejection device 8, which is not shown, is drawn out of the eye 9 (as indicated by the two arrows).

In this connection, it is for example advantageous if, to produce a throughflow cross section that is independent of its shape, the stent implant has additionally sealing, umbrella-like surfaces. After detachment from the implantation tool, the stent implant returns to its (expanded) initial shape, and additionally deploys the sealing, umbrella-like surfaces, as a result of which a cyclodialysis cleft in the tissue is additionally partially or completely sealed.

Figure 5:
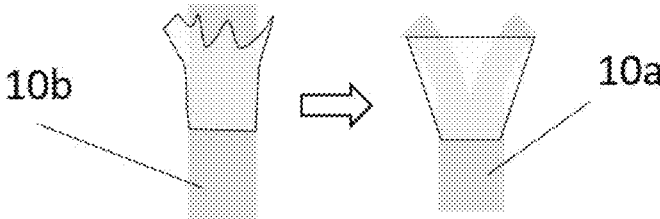
FIG. 5: depicts a stent implant with an umbrella-like surface for additional sealing in a compact and an expanded shape.

In this respect, FIG. 5 shows a stent implant with an umbrella-like surface for additional sealing.

Whereas the left-hand figure indicates the stent implant in its compact shape 10b with the surface not yet stretched out, the right-hand figure shows the deployed shape 10a with a stretched-out, umbrella-like surface.

As an alternative it is also possible, to produce a throughflow cross section that is independent of its shape, for the stent implant to have preperforated regions which can be severed only after insertion.

To that end, the stent implant, while largely retaining the compact shape, is first of all introduced into the target tissue and only later on, for example as required, is the change in shape triggered to fill out any tissue cleft. For example, the stent implant can be configured, via a preperforated zone that can be severed by application of a tool as required, such that a pretension present in the stent implant brings about the greater change in shape only after this severance. For example, a surgical lancet or a cutting laser, for example a focused femtosecond laser, would be suitable as severing tools.

The structures, layers or channels conducting the aqueous humor for example run parallel to the perforated surface in order that these structures, layers or channels stay behind upon subsequent severance. The severance of the perforated surfaces by use of a cutting tool can for example also be carried out ab interno by micro-incision of the cornea or the limbus with minimal invasion.

Figure 6:
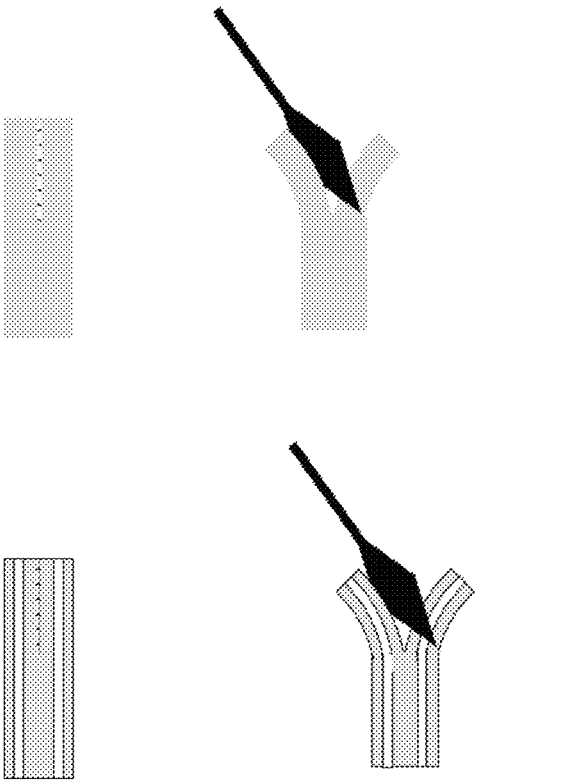
FIG. 6: depicts a stent implant with a preperforated region that can be severed only after insertion.

In this respect, FIG. 6 shows a stent implant with a preperforated region to be severed only after insertion, for example in order to enable additional sealing later on. Here, the upper image shows a stent implant of porous plastic with open pores and the lower figure shows a stent implant of a non-porous plastic through which channels pass (each in the closed and severed version).

In this respect, the intention is to produce a respective mechanical stress bringing about the change in shape in the implant. One option for producing such a material stress is that an implant present in an expanded initial shape, for example in a Y shape, is brought into its compact shape with the build up of material stress (i.e. bending or compressing) and is fixed in this shape by connecting parts of the implant (for example the arms of the Y), for example by welding or adhesive bonding.

Such a connection can then (similarly to the above-mentioned preperforated regions) be severed later on by application of suitable tools (for example lancets, laser or ultrasound) as required, in order to bring about the desired change in shape.

It is also possible for this connection of the parts of the implant to be soluble following a delay, with the result that the change in shape for the purpose of adaptation to the space available in the target tissue occurs automatically after a predefined period of time, even without renewed intervention. This can be achieved, for example, by water-, temperature- or light-soluble connecting structures. The soluble materials for example are nontoxic, colorless and can be resorbed by eye tissue. Examples are biodegradable polymers, but also fibrin glues suitable for adhesive bonding to tissues.

Such predefined periods of time for automatic dissolution of the connection can be seconds to months, for example 10 minutes to 5 days. In this case, it is possible to insert the implant in its compact shape without hindering the change in shape. Given periods of time with an interval of days, monitoring and evaluation of the aqueous humor outflow resistance before and after the change in shape is also possible, for example by daily measurements of the intraocular pressure, assuming that the production of aqueous humor is also similar at similar times of day.

In accordance with a particular example embodiment, the stent implant is designed to change shape following a time delay after introduction into the eye.

Connections and structures that dissolve following a delay, for example on the basis of known biodegradable polymers, are however also suitable for reducing throughflow resistances over time, for example by gradually opening up connections between pores or channel cross sections. This reduction in resistance can be desired in order to meet the drainage need, which increases predictably in the course of advancing glaucoma.

Such a change in shape of the stent implant by at least 20% following a time delay may be realized only after more than 1 hour, or after more than 1 week, or only after months or years through to decades have passed.

This change in the shape can happen in stages or continuously in order to reduce the throughflow resistance in the implant. This time-dependent reduction in throughflow resistance is suitable for all natural and artificial aqueous humor outflow pathways in the eye.

For example, such a time-dependent reduction in resistance would be realized by increasing the cross section as a result of structures gradually dissolving in the aqueous humor, for example channel or pore walls.

It should be noted here that the material dissolution rate is proportional to the respective surface size of the soluble structures that is wetted by aqueous humor, but also proportional to the respective local throughflow rate, both of which can change nonlinearly and in a time-dependent manner. In order to reduce the throughflow resistance over a certain period of time here, local variation in the solubility of the materials can also be used.

This dissolution would for example start, or have an effect, only after a certain period of time after implantation, when any pressure fluctuations owing to the implantation operation have subsided and stable pressure conditions have set in (approximately 1 to 3 months after the operation). It would be possible to realize this, for example, in that connections between channels or pores would additionally be completely formed only after dissolution of a certain wall thickness.

After this, it would be an option rather to reduce the throughflow resistance continuously by, for example, 5 to 10% per year over a period of time of for example 5 to 10 years, but at least over one year.

Figure 7:
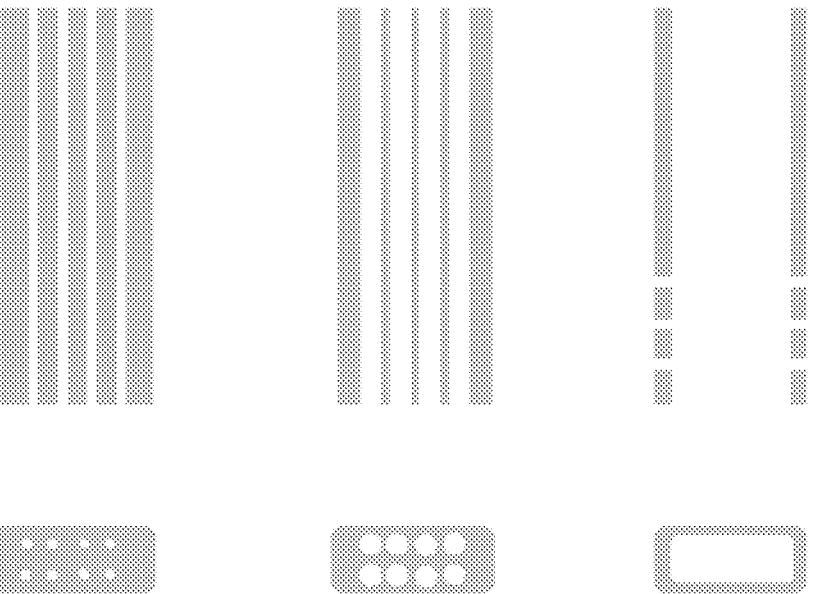
FIG. 7: depicts a stent implant, the change in shape of which following a time delay results in an enlargement of the throughflow cross section.

In this respect, FIG. 7 shows a stent implant, the change in shape following a time delay of which enlarges the throughflow cross section.

While the left-hand figure illustrates the pre- or intraoperative initial state, the middle figure shows a throughflow cross section that is already increased by a change in shape (after for example 1 year) and the right-hand figure shows the final state with a maximum cross section (after for example 10 years). As indicated in the right-hand figure, in extreme cases it is also possible to turn a three-dimensional lattice into a completely open tube and additionally form lateral tube openings.

Such structural changes in cross section would also be suitable for compensating or entirely preventing any reductions in cross section, or increases in throughflow resistance, owing to closures of pores or channels as a result of tissue cells growing into the implant.

In accordance with a further example embodiment, the stent implant includes plastic, the physical and/or chemical properties of which can be locally varied by reworking in order to change inflow and outflow cross sections and/or resistances. Thus, it would be possible to close (for example by fusion) or open (for example by laser disruption) pores or channels in certain regions, for example, by reworking (for example using a laser), in order to adapt the implant to the pressure reduction requirements of a patient. This can be done preoperatively outside of the patient's eye, or else intra- or postoperatively in the target tissue.

For example, for the stent implants according to the invention, use is made of silicones, polyamide, polyurethane or polyethylene as plastics that have locally different chemical and/or physical, in particular mechanical properties and are used individually or in combination.

This local variation in the properties of the plastics can be achieved by coating various feedstocks. Here, for example, sponge-like plastics with very different pore sizes are also conceivable, as are plastics of which the chemical and/or physical properties have been locally changed. Examples that can be mentioned are laser cutting, laser ablation, plasma etching, elution, polymerization by irradiation, or else local shrinkage by heating.

Such local variation in the material properties also makes it possible to realize, for example, a mixed shape of a stent implant, through which channels pass, with open pores within throughflow channels. This can be desirable in order to realize defined throughflow resistances for the draining aqueous humor that do not depend or depend only very little on the change in shape. Such limiting throughflow resistances can serve, for example, as an alternative to limiting large throughflows, if a deep cyclodialysis cleft, which has an excessively great drainage capability for the pressure reduction that is sought, were to form in the tissue behind the stent implant (as seen in the direction of the anterior chamber).

Hydrophilization of the implant material in certain regions can also be used to build up desired mechanical stresses by water retention (swelling), which are required for a later change in shape after preperforated regions or connections that dissolve under the influence of water have been severed.

Instead of silicones, it is also possible to use other biocompatible polymers. Braids or sponges of metal materials, such as steel or nitinol, can also be used, it being necessary to generate sufficient residual elasticity to adapt the shape after the implant stent has been ejected from the tool.

In the stent implant according to the invention, it is furthermore additionally possible, as is known from the prior art, to integrate sensor systems for measuring pressure and/or glucose.

The solution according to the invention provides a stent implant for treating glaucoma, by use of which stent implant the drainage of aqueous humor from the anterior chamber into the suprachoroidal space can be realized. A reduction in pressure which is as consistent as possible is achieved by the stent implant according to the invention. Moreover, the stent implant is suitable for closing a cleft that has possibly opened up in the suprachoroidal space such that no outflow, or only very limited outflow, of aqueous humor around the implant can occur.

The use of material which is elastic at least at times makes it possible to insert the stent implant into the anterior chamber ab interno by micro-incision of the cornea or the limbus and position it correspondingly for the drainage of aqueous humor into the suprachoroidal space.

The invention claimed is:

1. A stent implant for treating glaucoma by drainage of aqueous humor from an anterior chamber of an eye, wherein:

the stent implant is structured to enable a change in shape of the stent implant after introduction into the eye, which change involves increasing a width, a thickness, a throughflow cross section or a combination of the foregoing at least at one point on the stent implant by at least 20%, wherein the stent implant, including a shape thereof, a cross section or both, are structured to establish inflow and outflow zones of the implant such that a through-flow cross section predominantly independent of the shape is achieved.

2. The stent implant as claimed in claim 1, further wherein the increasing the width, the thickness, the throughflow cross section or a combination of the foregoing at least at one point on the stent implant is selected from a group consisting of by more than 200% and by more than 400%.

3. The stent implant as claimed in claim 1, wherein the stent implant is structured such that the changes in the width and the thickness differ by at least 50%.

4. The stent implant as claimed in claim 1, wherein the stent implant is structured to change the resistance to flow of the aqueous humor through the stent implant is selected from a group consisting of by less than 50%, by less than 20% and by less than 10%, when the stent implant changes shape.

5. The stent implant as claimed in claim 1, wherein the stent implant has a tubular shape or another shape selected from a group consisting of a Y, X, U, N, A, V, W or O shape.

6. The stent implant as claimed in claim 1, wherein the stent implant comprises an elastic, sponge-like, open-pore or non-porous plastic.

7. The stent implant as claimed in claim 6, wherein the elastic, sponge-like, open-pore or non-porous plastic is selected from a group consisting of silicone, polyurethane and polyamide.

8. The stent implant as claimed in claim 1, wherein the stent implant comprises only one plastic or is a composite of multiple plastics with different chemical properties, physical properties, mechanical properties or a combination thereof.

9. The stent implant as claimed in claim 1 wherein the stent implant at least partially comprises a hydrophilic plastic in order, after introduction, to cause the stent implant to change shape by taking up water.

10. The stent implant as claimed in claim 1, wherein the stent implant comprises a material which has a memory effect, in order to cause it to change shape or adapt its shape at body temperature.

11. The stent implant as claimed in claim 1, wherein, to produce an optional change in shape, the stent implant comprises additional preperforated regions which can be severed only after insertion.

12. The stent implant as claimed in claim 11, wherein the stent implant is structured such that the connection dissolves after seconds, or after weeks, or only after months have passed.

13. The stent implant as claimed in claim 1, wherein the stent implant comprises at least one connection which dissolves following a delay with a result that the change in shape for the purpose of adaptation to the space available in the target tissue occurs automatically.

14. The stent implant as claimed in claim 1, wherein the stent implant is structured to change shape following a time delay after introduction into the eye.

15. The stent implant as claimed in claim 1, wherein the stent implant is structured such that the shape change by at least 20% following a time delay only after more than 1 hour, or after more than 1 week, or only after months or years have passed.

16. The stent implant as claimed in claim 1, wherein the stent implant comprises plastic, physical or chemical properties or both of which can be locally varied by reworking in order to adapt inflow and outflow cross sections or throughflow resistances or mechanical stresses or a combination thereof.

17. The stent implant as claimed in claim 1, further comprising sensor systems that measure pressure, glucose or both.

18. The stent implant as claimed in claim 1, wherein the stent implant comprises an elastic, open-pore or non-porous metal material.

19. The stent implant as claimed in claim 18, wherein the elastic, open-pore or non-porous metal material is selected from a group consisting of titanium, steel and nitinol.

20. A stent implant for treating glaucoma by drainage of aqueous humor from an anterior chamber of an eye, wherein:

the stent implant is structured to enable a change in shape of the stent implant after introduction into the eye, which change involves increasing a width, a thickness, a throughflow cross section or a combination of the foregoing at least at one point on the stent implant by at least 20%, wherein, to produce the throughflow cross section that is independent of shape, the stent implant additionally comprises sealing, umbrella-like surfaces.

* * * * *